United States Patent
Anson et al.

(10) Patent No.: US 6,814,747 B2
(45) Date of Patent: *Nov. 9, 2004

(54) SURGICAL GRAFT/STENT SYSTEM

(76) Inventors: Anthony Walter Anson, Anson Medical Limited, The Innovation Centre, 68 Milton Park, Middlesex (GB), TW4 7EZ; Peter Phillips, Anson Medical Limited, The Innovation Centre, 68 Milton Park, Abingdon (GB), OX14 4RX; Julian Ellis, 68 Carlton Road, Nottingham (GB), NG3 2AP; Alan McLeod, Pearsalls Implants, Tancred Street, Taunton, Somerset (GB), TA1 1RY; Gail Beaton, 18 Greys Hill, Henley on Thames, Oxon (GB), RG9 1SJ; Peter Butcher, 68 Carlton Road, Nottingham (GB), NG3 2AP (*) Notice: Subject to any disclaimer, the term of this patent is extended or adjusted under 35 U.S.C. 154(b) by 11 days.

This patent is subject to a terminal disclaimer.

(21) Appl. No.: 09/999,870

(22) Filed: Oct. 19, 2001

(65) Prior Publication Data

US 2002/0082674 A1 Jun. 27, 2002

Related U.S. Application Data

(63) Continuation-in-part of application No. 09/601,023, filed on Jul. 26, 2000, and a continuation-in-part of application No. 09/036,588, filed as application No. PCT/GB99/00261 on Jan. 26, 1999, now Pat. No. 6,334,867.

(30) Foreign Application Priority Data

Sep. 6, 1996 (WO) .............................. PCT/GB96/02212
Jan. 26, 1998 (GB) .............................................. 9801660
Jan. 31, 1998 (GB) .............................................. 9802060

(51) Int. Cl.$^7$ .................................................. A61F 2/06
(52) U.S. Cl. ..................... 623/1.13; 623/1.16; 623/1.35
(58) Field of Search ............................... 623/1.13, 1.14, 623/1.15–1.2, 1.32, 1.35

(56) References Cited

U.S. PATENT DOCUMENTS

| 4,800,882 A | | 1/1989 | Gianturco |
| 4,907,336 A | | 3/1990 | Gianturco |
| 4,994,071 A | * | 2/1991 | MacGregor ................. 606/194 |
| 5,041,126 A | | 8/1991 | Gianturco |

(List continued on next page.)

FOREIGN PATENT DOCUMENTS

| DE | 44 46 036 A1 | 12/1994 |
| DE | 195 33 589 A1 | 3/1996 |
| EP | 0 326 426 A2 | 8/1989 |
| EP | 0 461 791 A1 | 12/1991 |
| EP | 0 508 473 A2 | 10/1992 |
| EP | 0 621 017 A1 | 10/1994 |
| EP | 0 757 904 A1 | 2/1997 |
| EP | 0 759 287 A1 | 2/1997 |
| FR | 2 694 688 A1 | 2/1994 |
| WO | WO 97/09007 | 3/1997 |
| WO | WO 97/33532 | 9/1997 |
| WO | WO 99/37242 | 7/1999 |

*Primary Examiner*—David J. Isabella
*Assistant Examiner*—Hieu Phan
(74) *Attorney, Agent, or Firm*—Craig A. Fieschko, Esq.; DeWitt Ross & Stevens S.C.

(57) ABSTRACT

A tubular graft/stent comprises a tubular sheath having at intervals along its length a plurality of ring-like rigid members, which are attached to the sheath around their respective circumferences and are made of a shape memory material, so that when the members change shape the sheath adopts a new cross section in conformity with the members along the sheath's whole length. The members may be discontinuous to allow the adoption of a contracted shape in the martensitic phase and an expanded shape in the austenitic phase. A graft may also have a branched side tube which can be inverted so as to be housed within the sheath.

18 Claims, 4 Drawing Sheets

U.S. PATENT DOCUMENTS

| | | | |
|---|---|---|---|
| 5,167,614 A | | 12/1992 | Tessmann et al. |
| 5,314,444 A | | 5/1994 | Gianturco |
| 5,342,387 A | * | 8/1994 | Summers .................... 606/198 |
| 5,639,278 A | * | 6/1997 | Dereume et al. .......... 623/1.13 |
| 5,653,743 A | | 8/1997 | Martin |
| 5,700,285 A | | 12/1997 | Myers et al. |
| 5,709,713 A | * | 1/1998 | Evans et al. ............... 623/1.53 |
| 5,755,770 A | | 5/1998 | Ravenscroft |
| 5,782,904 A | | 7/1998 | White et al. |
| 5,800,515 A | | 9/1998 | Nadal et al. |
| 5,824,040 A | | 10/1998 | Cox et al. |
| 5,833,707 A | | 11/1998 | McIntyre et al. |
| 5,948,018 A | | 9/1999 | Dereume et al. |
| 6,187,033 B1 | | 2/2001 | Schmitt et al. |
| 6,334,867 B1 | * | 1/2002 | Anson ....................... 623/1.13 |
| 6,352,561 B1 | * | 3/2002 | Leopold et al. ............ 623/1.23 |

\* cited by examiner

US 6,814,747 B2

SURGICAL GRAFT/STENT SYSTEM

CROSS-REFERENCE TO RELATED APPLICATIONS

This application is a continuation-in-part of U.S. patent application Ser. No. 09/036,588 filed Mar. 6, 1998 (now U.S. Pat. No. 6,334,867) and U.S. patent application Ser. No. 09/601,023 filed Jul 26, 2000, which is a 371 of PCT/GB99/00261 filed Jan. 26, 1999, both of which are incorporated by reference herein.

FIELD OF THE INVENTION

This invention relates to a graft/stent system for use in human or animal surgery.

BACKGROUND OF THE INVENTION

One example of a type of graft/stent similar to the one discussed in this document is disclosed in EP 0326426A, which describes an artificial blood vessel in the form of a tubular sheath having a ring-like member located at each of its two ends.

Another example, disclosed in EP 0461791A, is an aortic graft with one of its tubular ends divided into two branches.

WO 99/37242 (USSN 09/036,588), the contents of which are incorporated herein by reference, discloses a reinforced graft formed from a flexible sheet of graft material to which is sewn a reinforcing wire. The graft/stent may be formed flat, then rolled into a tube and secured. The reinforcing wire is preferably sewn to the sheet in a ladder of substantially straight portions connected by substantially U-shaped connection portions.

SUMMARY OF THE INVENTION

To give the reader a basic understanding of some of the advantageous features of the invention, following is a brief summary of preferred versions of the graft/stent. As this is merely a summary, it should be understood that more details regarding the preferred versions may be found in the Detailed Description set forth elsewhere in this document. The claims set forth at the end of this document then define the various versions of the invention in which exclusive rights are secured.

In one preferred version of the invention, a tubular sheath defines a graft/stent. A flexible integral branch tube is also provided, with an end fixed to the tubular sheath at an opening in a side wall of the tubular sheath. The branch tube is a graft/stent along its entire length, and can be fully inverted along its entire length so as to be fully housed within the tubular sheath during an insertion operation in a human or animal body, and redeployed as a branch within the body after the insertion operation. The tubular sheath and/or the branch tube are preferably graft/stents as disclosed in WO 99/37242.

Preferably, the tubular sheath and/or the branch tube has filamentary reinforcing material (such as nitinol wire) attached thereto to provide support within the body. In a particularly preferred embodiment, the reinforcing material constitutes up to 10% of the diameter of the tubular sheath or the branch tube, with an amount of around 1% being particularly preferred. The bend diameter of the reinforcing material is preferably up to 10% (and most preferably about 5%) of the diameter of the tubular sheath or the branch tube. These parameters of the reinforcing material allow the branch tube to evert within the tubular sheath.

The tubular sheath preferably has at intervals along its length a plurality of rigidizing ring-like support members attached to the sheath around their respective circumferences and which are made of a shape memory material, so that when the members change shape, the sheath adopts a new cross-section in conformity with them along its whole length. This arrangement defines a compliant tubular sheath into which a series of open rings are integrated, wherein the rings act as rigidizing members and are capable of being radially compressed by mechanical forces in the martensitic phase so as to reduce the diameter, and which may returning in the austenitic phase to a memorized, larger diameter by a thermal effect.

The invention also relates to a tubular sheath having a branch tube which is sufficiently flexible to be inverted so as to be housed within the sheath during an insertion operation in a human or animal body, and to be redeployed as a branch after the operation. The sheath and/or the branch tube may employ annular support members (preferably rigidizing members) of a shape memory material, as explained above. In all cases, the members may be discontinuous, e.g. a ring with a break so as to facilitate compression and re-expansion.

Further advantages, features, and objects of the invention will be apparent from the following detailed description of the invention in conjunction with the associated drawings.

DETAILED DESCRIPTION OF PREFERRED EMBODIMENTS OF THE INVENTION

Figure 1:
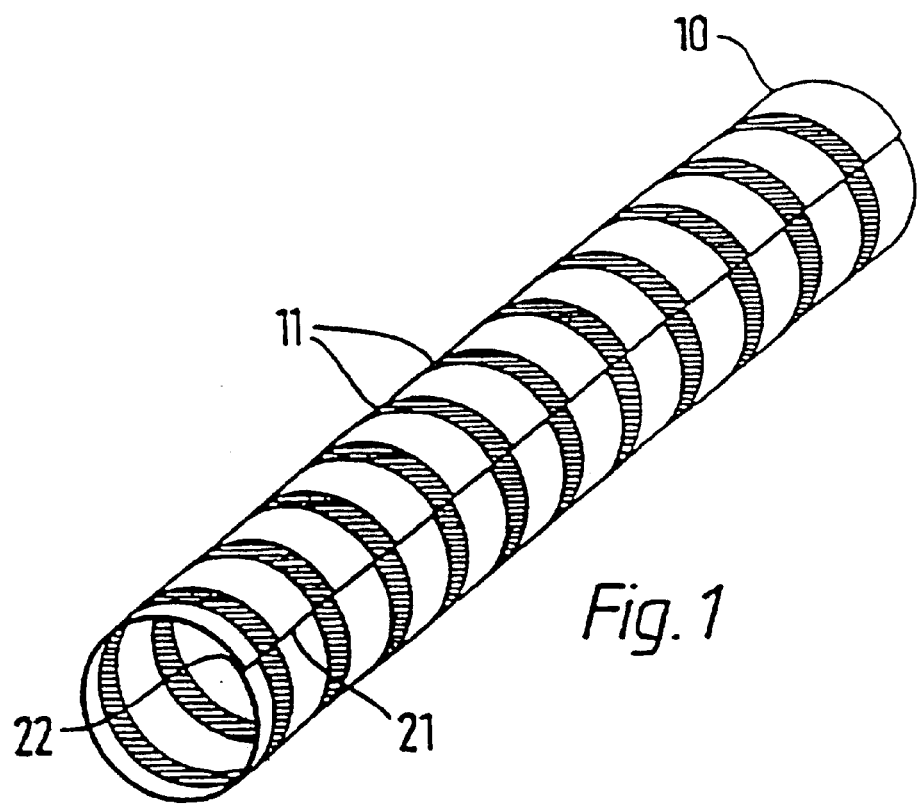
FIG. 1 shows a perspective view of a first form of graft.

An exemplary general arrangement is shown in FIG. 1. A compliant tube 10 can be constructed of any flexible material such as cloth, polymers, elastomers or gels. Secured within or on the surface of the compliant tube are a plurality of expandable or contractible open rings 11 composed of shape memory alloy material. The shape memory alloy rings give structural support to the compliant tubular sheath and are oriented transverse to the axis of the tube. The tube is circumferentially closed by the overlap 20, but has free edges 21, 22. Alternatively, the edges 21, 22 might abut one another, but this does not provide as much certainty that the tube wall is closed.

The compliant tube 10 can be generated by tube fabrication methods, or an "open" tube could be made by using flat sheets whose shape is established by the shape memory alloy rings. The tubular form might also use sheets of dissimilar materials, e.g., an inner sheet having a different coefficient of thermal expansion than an abutting coplanar outer sheet, whereby contraction of the inner sheet and/or expansion of the outer sheet causes the sheets to curl into the tubular form. The tube may be produced in continuous lengths and cut off as needed.

The shape memory alloy rings can be retained by casting a suitable compliant tube material around the rings, and/or by adhesive bonding, sewing, or generating a series of pockets within which the rings may be held by welding, sewing, mechanical fixation or adhesive bonding. In the embodiment shown, the rings 11 are each formed in a single piece, but could instead each be formed in two or more arcuate sections with abutting or overlapping ends.

Figure 2:
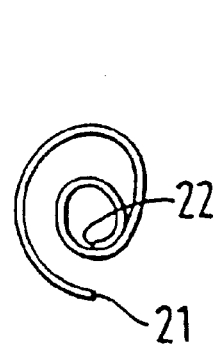
FIG. 2 shows its compressed form in the martensitic phase in transverse cross-section.
Figure 3:
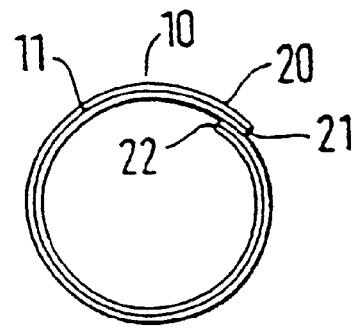
FIG. 3 shows its expanded form in the austenitic phase.

FIGS. 2 and 3 show the compressed (e.g. spiral or rolled-up) and expanded forms of the tube. As an example, the tubular graft/stent might be radially compressed down to 5.5 mm outside diameter before the device is fitted into the human body via a delivery catheter. In its expanded form, the outside diameter might be up to 4 cm.

The device described is suitable for a number of minimally invasive surgical techniques, or may substantially reduce trauma associated with the introduction of implanted medical devices within a living organism. A single, plain tube (known as a tubular graft) with integrated expandable/contractible rings (known as stents) as described is inserted into an occluded fluid carrying vessel or a vessel that has a stricture. When appropriately positioned via the catheter, heat from the human body (or a heated fluid introduced) will cause the latent geometry of the shape memory alloy to be recalled. Under these circumstances the rings will expand to a pre-determined position as seen in FIG. 3, the outside dimensions of which will be slightly larger than the inner dimensions of the fluid carrying vessel. Frictional effects will normally retain the graft/stent in position. However, the shape memory alloy may be arranged so that when a thermal transition point (memory recall) is reached, selected sections of the rings/stents will protrude from the tube's surface, presenting a substantial fixation force. This retention feature may be provided in one or more of the alloy rings.

This device may find applications in surgical repair or maintenance procedures for the human body or other animal species. Gastrointestinal system connections, esophageal cancer, aneurysms, coronary bypass connections and other vascular bypass or shunt procedures could employ the stent/graft device.

The dynamic properties of the rings expand the graft/stent within the body to effect an opening of constricted or occluded vessel. The outer graft sheath would assist in preventing occlusive material from once again entering the vessel. The compliant sheath will also exclude tumorous growth, maintaining luminal patency.

Figure 4:
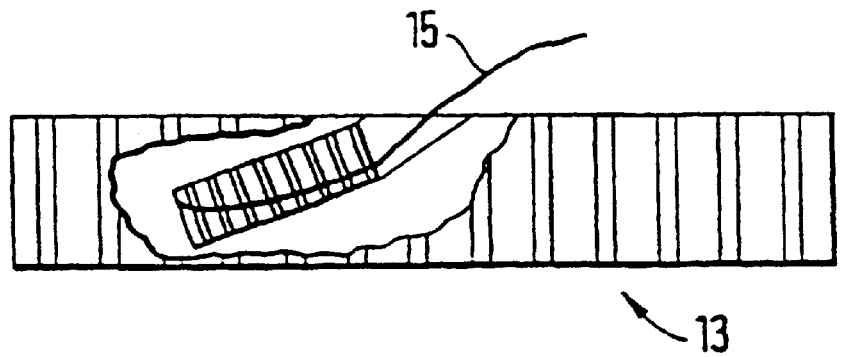
FIG. 4 shows an embodiment having a branch tube in its inverted position.
Figure 5:
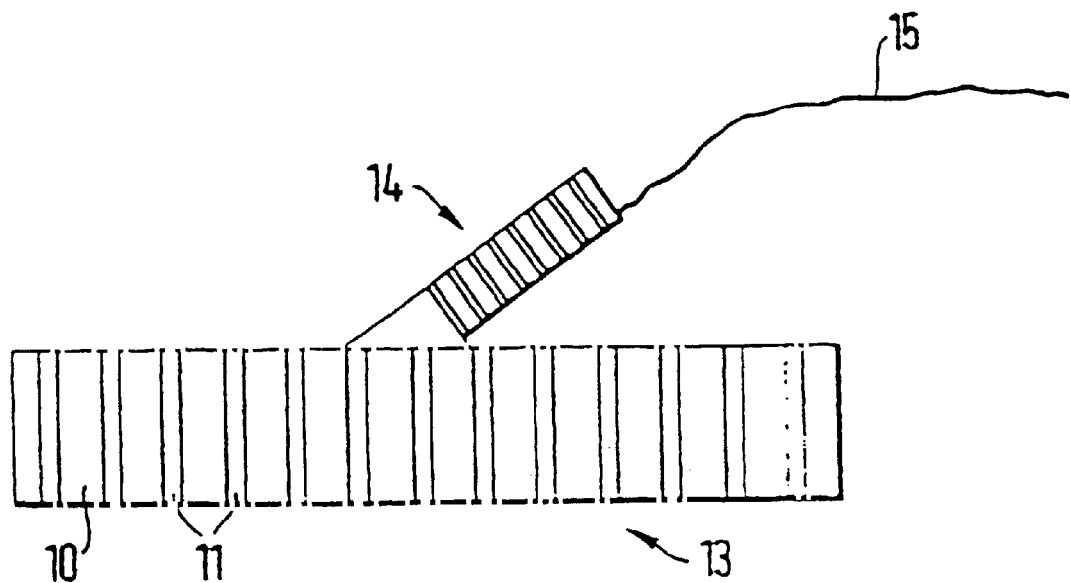
FIG. 5 shows the FIG. 4 version with the branch tube deployed.

The tubular graft with integrated shape memory alloy rings may be a simple tube-like form as described, or could instead be a manifold system having a main tube 13 from which one or substantial numbers of branches/connections 14 may be made, as seen in FIGS. 4 and 5. The single tube or manifold will allow fluids to pass in or out of the the branches, to or from the main tube structure. The branches extending from the main body can be of uniform cross-section or of tapering construction.

A tubular graft of the type described might be simply bifurcated, or may have numerous smaller or larger tubes of similar construction attached to the main tube body. The branches attached to the body of the device may have a similar shape memory alloy ring configuration. Each branch 14 can be inverted so as to fit within the main tube. Under these conditions, the whole assembly can be radially compressed, the manifold system now appearing as a single tube for initial insertion via a catheter. A suitable cord 15 is connected to the inverted branch enabling it/them to be re-inverted by pulling the cord, as shown in FIG. 5. Preferably, the rings nearer to the main tube are largest and are progressively smaller towards the end, to allow the inversion to occur.

When warmed, the shape memory alloy rings will expand to a pre-determined position. If employed in a surgical repair, forces exerted by the shape memory alloy rings will be of sufficient magnitude to open an occluded vessel, thus enabling appropriate fluid flows to continue.

The compliant outer sheath would enable radial or axial movement of the vessel to occur. This might be the case if the stent/graft were positioned in an esophagus that had radially disposed tumors. Peristalsis effects used to assist transportation of food and liquids in the human body would need to be maintained in esophageal dysfunctional problems. The covered or sheathed stent system would exclude tumorous in-growth and still enable peristalsis to occur.

The compliant material could be 0.050 mm polyurethane, polyester or polythene. The shape memory material may be a metal alloy with this property, or alternatively certain moldable plastics materials such as homopolymers of lactide or glycolide, or copolymers of lactide and glycolide.

The invention is also considered to include a graft with a side tube which does not employ stents of shape memory material. Thus, in addition to shape memory materials, the ring-like support members 11 can also be fabricated from elastic materials such as stainless steel or the super-elastic forms of nickel-titanium alloys. In this case, the implant is constrained within an outer sheath after whose removal the graft will expand to adopt its final shape.

Figure 6:
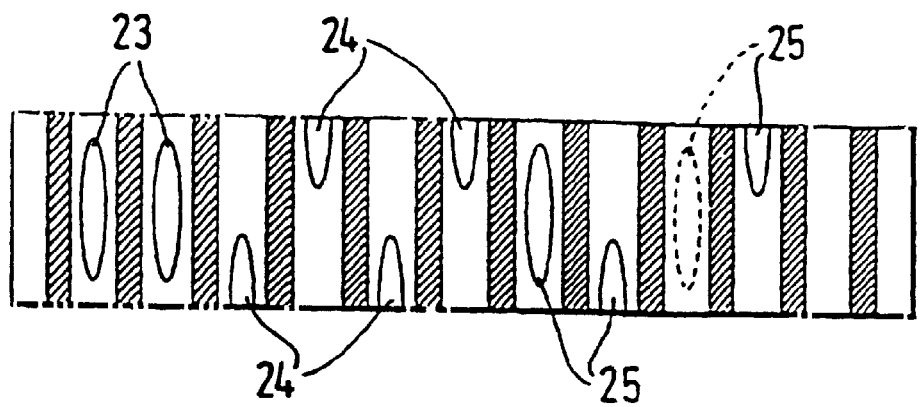
FIG. 6 shows a further embodiment of the present invention.

In the embodiment of FIG. 6, which is of particular benefit in stenting tortuous vessels such as the male urethra, the flexible tubular sheath can contain slits or openings 23 which are approximately parallel to the ring-like members and which allow greater flexion of the implant without kinking the sheath. The arrangement of the slits or openings can be varied with the application and can be positioned to be all on one side of the tube 23, on alternating sides 24 or spirally arranged along the sheath (25). Other arrangements are possible.

Referring back to the overlap 20 of FIG. 3, the overlap 20 can be designed to have one of three properties:

1) The overlap can be left to slide freely over itself, permitting the graft assembly to be contracted by muscles in the vessel or to allow pressure pulses in arterial blood, arising from the heartbeat, to be transmitted to the artery wall. The action of pressure pulses is involved in maintaining the vasomotor tone in blood vessels. The mating surfaces of the overlapping part of the sheath can be coated with materials such as PTFE or diamond-like coatings to reduce friction and wear.

Figure 7:
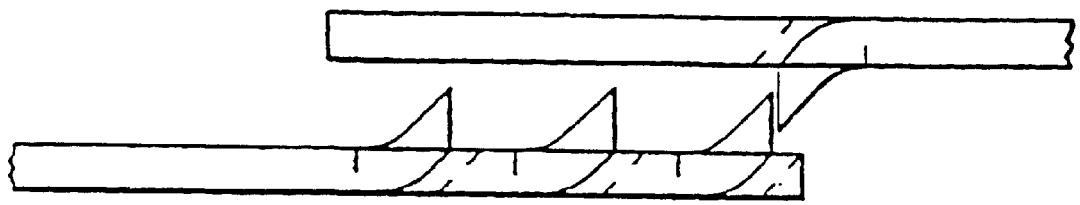
FIGS. 7 and 8 show enlarged and developed views of two versions of an overlap region.

2) As shown in FIG. 7, the overlap can incorporate a ratchet-like mechanism which will allow the diameter of the ring-like rigid member to expand, but not to contract. This will guarantee that the lumen of the vessel will be maintained to a minimum diameter and will allow the ring to be locked against the inside of the vessel wall to prevent migration of the device.

Figure 8:
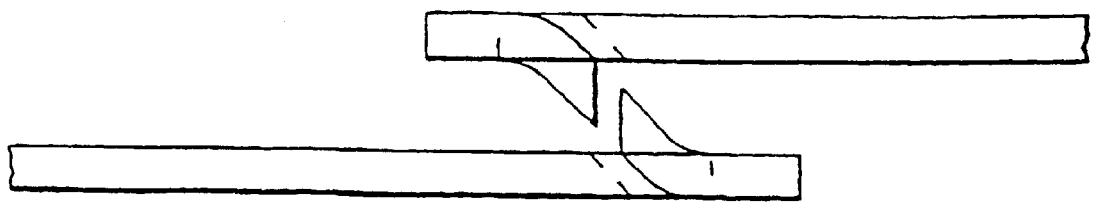

3) As shown in FIG. 8, the overlap can incorporate a ratchet-like mechanism which will allow the diameter of the ring-like rigid member not to exceed a specified diameter. This is of use where the vessel is fragile and can be exposed to high intraluminal pressures.

The ratchet-like mechanism can be incorporated onto the walls of the sheath by molding, machining, or attaching ratchet components. Alternatively, the ratchet mechanism can be formed in the ends of the ring-like member and can be either permanently present, or deployed by the action of thermal memory.

An implant can be assembled which incorporates a combination of all three types of overlap mechanism so that (for example) the distal ends of the graft can use ratchet expanding rings to lock the device in place, while the main body of the graft uses alternating sliding and diameter-limiting rings to allow limited transmission of pulsatility while restricting the maximum diameter of the graft.

The benefit of the graft can be increased by incorporating coatings onto its inner or outer surfaces. These coatings can be biomimetics such as phosphorylcholines and proteins, organic biocompatibles such as hydrophillic plastics, and inorganic coatings such as diamond-like carbon. The coatings can be used to be thrombus-resistant, encrustation-resistant, or to promote cellular ingrowth. In addition, the coatings can be used to release locally acting pharmacological agents, and they can be multiply layered.

Deployment of the inverted segment 14 can be achieved by adding a short handle, tab or strip to the distal end of the side branch which can be engaged by a snare, forceps or similar engagement means.

Figure 9:
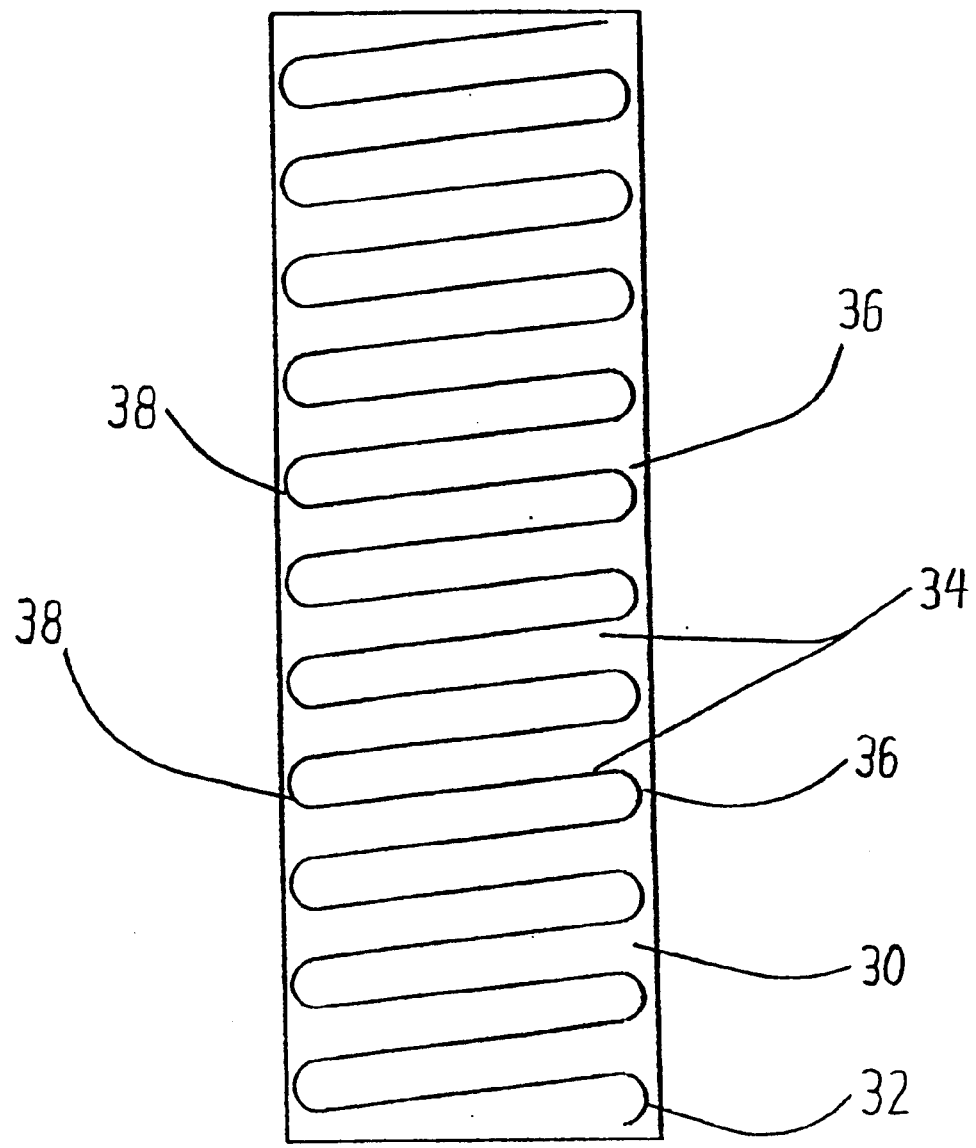
FIG. 9 shows an alternative version of a sheet suitable for formation into a graft (as in FIGS. 1–3) wherein the sheet includes reinforcement material formed from a filament sewn into a ladder of substantially straight portions connected by substantially U-shaped connection portions.

The invention may also make use of sheets such as those illustrated in FIG. 9, wherein the graft (shown in its unrolled state) includes a sheet of flexible material 30 (such as cloth, polymers, elastomers, etc.) of the type used for grafts. The sheet 30 bears reinforcing material 32 in the form of a wire, strip, or similar elongated flexible filamentary form. The reinforcing filament 32 is preferably pre-arranged in a substantially flat ladder pattern in which the straight portions 34 of the filament 32 may lie either perpendicular to the longitudinal axis of the sheet 30 or at a slight angle to the normal to this axis. In use, the sheet 30 is rolled into a tube such that the opposed rounded ends 36, 38 of the filament 32 become located adjacent to one another (as in FIG. 1). When the straight portions 34 of the filament lie perpendicular to the longitudinal axis of the sheet 30, the rounded loops 36, 38 of the filament 32 interdigitate. On the other hand, when the straight portions 34 of the filament 32 are disposed at the appropriate angle to the perpendicular, the opposing rounded loops 36, 38 can be made to oppose or overlap one another.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. Thus, the invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A graft/stent comprising:
   a. a tubular sheath; and
   b. a flexible branch tube having an end fixed to the tubular sheath at an opening in a side wall of the tubular sheath, wherein the branch tube can be fully inverted along its entire length so a to be fully housed within the tubular sheath during an insertion operation in a human or animal body, and redeployed as a branch within the body after the insertion operation.

2. A graft/stent according to claim 1, wherein the branch tube has filamentary reinforcement material attached along its length.

3. A graft/stent according to claim 2, wherein the diameter of the reinforcement material is up to 10% of the diameter of the branch tube.

4. A graft/stent according to claim 2, wherein the filamentary reinforcement material is attached along the length of the branch tube in a series of substantially linear circumferential hoops spaced apart longitudinally along the branch tube, each of the hoops being joined by connecting portions of reinforcement material.

5. A graft/stent according to claim 4, wherein the filamentary reinforcement material is formed from a single wire.

6. A graft/stent according to claim 4, wherein the reinforcement material is formed from a filament formed into a ladder of substantially straight portions connected by substantially U-shaped connection portions.

7. A graft/stent according to claim 4, wherein the connecting portions of reinforcement material have a bend diameter which is up to 10% of the diameter of the branch tube.

8. A graft/stent according to claim 4, wherein the diameter of the reinforcement material is up to 10% of the diameter of the branch tube.

9. A graft/stent according to claim 1, wherein the tubular sheath has filamentary reinforcement material attached along its length.

10. A graft/stent according to claim 1, wherein the tubular sheath has filamentary reinforcement material attached along its length in a series of hoops spaced along the tubular sheath, each of the hoops being joined by connecting portions of reinforcement material.

11. A graft/stent according to claim 10, wherein the filamentary reinforcement material is formed from a single wire.

12. A graft/stent according to claim 10, wherein the reinforcement material is formed from a filament formed into a ladder of substantially straight portions connected by substantially U-shaped connection portions.

13. A graft/stent comprising:
    a. a sheet of material having one or more affixed filaments, the filaments being formed into a ladder of substantially straight portions connected by substantially U-shaped connection portions; and
    b. a flexible branch tube having an end opening through the sheet, wherein the branch tube can be fully inverted along its entire length to rest on either side of the sheet, wherein the sheet may be formed into a tubular sheath.

14. The graft/stent of claim 13 wherein the branch tube is formed of an at least partially rolled sheet of material having one or more affixed filaments, the filaments being formed into a ladder of substantially straight portions connected by substantially U-shaped connection portions.

15. A graft/stent comprising:
    a. a tubular sheath; and
    b. a flexible branch tube having an end fixed to the tubular sheath at an opening in a side wall of the tubular sheath, wherein the branch tube is formed of an at least partially rolled sheet of material having one or more affixed filaments, the filaments being formed into a ladder of substantially straight portions connected by substantially U-shaped connection portions.

16. The graft/stent of claim 15 wherein the branch tube can be fully inverted along its entire length so as to be fully housed within the tubular sheath during an insertion operation in a human or animal body, and redeployed as a branch within the body after the insertion operation.

17. The graft/stent of claim 15 wherein the tubular sheath is formed of a sheet of material having one or more affixed filaments, the filaments being formed into a ladder of substantially straight portions connected by substantially U-shaped connection portions.

18. The graft/stent of claim 15 wherein the branch tube can be fully inverted along its entire length so as to be fully housed within the tubular sheath during an insertion operation in a human or animal body, and redeployed as a branch within the body after the insertion operation.

* * * * *